(12) United States Patent
Matute Almau et al.

(10) Patent No.: US 7,651,836 B2
(45) Date of Patent: Jan. 26, 2010

(54) METHODS FOR DIAGNOSIS AND PROGNOSTIC OF PSYCHIATRIC DISEASES

(75) Inventors: Carlos Matute Almau, Leioa (ES); Aitor Palomino Fernández de Larrea, Vitoria (ES); Ana González Pinto, Vitoria (ES)

(73) Assignees: Hospital Santiago Apóstol, Gasteiz (Victoria) (ES); Universidad Del País Vasco, Leioa (Vizcaya) (ES)

( * ) Notice: Subject to any disclaimer, the term of this patent is extended or adjusted under 35 U.S.C. 154(b) by 0 days.

(21) Appl. No.: 11/775,525

(22) Filed: Jul. 10, 2007

(65) Prior Publication Data

US 2008/0081334 A1 Apr. 3, 2008

(30) Foreign Application Priority Data

Aug. 4, 2006 (ES) ................................ 200602139

(51) Int. Cl.
*G01N 33/50* (2006.01)
*G01N 33/53* (2006.01)

(52) U.S. Cl. .......................................... 435/4; 435/7.1
(58) Field of Classification Search ........................ None
See application file for complete search history.

(56) References Cited

OTHER PUBLICATIONS

Siuciak et al. Pharm. Biochem. Behavior, vol. 56, pp. 131-137, 1997.*
Palomino et al., "Decreased Levels of Plasma BDNF in First-Episode Schizophrenia and Bipolar Disorder Patients," Schizophrenia Research, vol. 86, (2006), pp. 321-322.
Pirildar, Sebnem, et al., Low serum levels of brain-derived neurotrophic factor in patients with schizophrenia do not elevate after antipsychotic treatment, Science Direct, Progress in Neuro-Psychopharmacology & Biology Psychiatry, 2004, pp. 709-713, vol. 28.
Jockers-Scherubl, Maria C., et al., Brain-derived neurotrophic factor serum concentrations are increased in dug-naive schizophrenic patients with chronic cannabis abuse and multiple substance abuse, Science Direct, Neuroscience Letters, 2004, pp. 79-83, vol. 371.
Toyooka, Kazuhiko, et al., Decreased levels of brain-derived neurotrophic factor in serum of chronic schizophrenic patients, Psychiatric Research, 2002,pp. 249-257, vol. 110.
Berry, Neeraj, et al., Molecular genetics of schizophrenia: a critical review, J Psychiatry Neurosci, 2003, pp. 415-429, vol. 28(6).
Corfas, Gabriel, et al., Neuregulin 1-erbB signaling and the molecular/cellular basis of schizophrenia, Nature Neuroscience, Jun. 2004, pp. 575-580, vol. 7, No. 6.
Schumacher, Johannes, et al., Genomewide Scan and Fine-Mapping Linkage Studies in Four European Samples with Bipolar Affective Disorder Suggest a New Susceptibility Locus on Chromosome 1p35-p36 and Provides Further Evidence of Loci on Chromosome 4q31 and 6q24, The American Society of Human Genetics, 2005, pp. 1102-1111, vol. 77.
Liu, Hsing-Cheng, et al., Immunologic variables in acute mania of bipolar disorder, Journal of Neuroimmunology, 2004, pp. 116-122, vol. 150.
Tsai, Shang-Ying, et al., Plasma levels of soluble transferrin receptors and Clara cell protein (CC16) during bipolar mania and subsequent remission, Journal of Psychiatric Research, 2003, pp. 229-235, vol. 37.
Baker, Ivory, et al., Serum cytokine concentrations in patients with schizophrenia, Schizophrenia Research, 1996, pp. 199-203, vol. 20.
Gonzalez-Pinto, A., et al., Age-dependence of Schneiderian psychotic symptoms in bipolar patients, Schizophrenia Research, 2003, pp. 157-162, vol. 61.
Durany, N., et al., Neurotrophic factors and the pathophysiology of schizophrenic psychoses, Eur Psychiatry, Sep. 2004, Abstract, vol. 19(6).
Freedman, R., et al., Early biomarkers of psychosis, Dialogues Clin Neurosci, 2005, Abstract, vol. 7(1).

* cited by examiner

*Primary Examiner*—Jeffrey Stucker
*Assistant Examiner*—Stephen Gucker
(74) *Attorney, Agent, or Firm*—Tristan A. Fuierer; Moore & Van Allen, PLLC

(57) ABSTRACT

The invention describes an in vitro method for detecting a psychiatric disorder occurring with psychosis selected from schizophrenia and bipolar disorder in an individual who has suffered a first psychotic episode, or for determining the state or severity of said disorder, or for monitoring the effect of a therapy administered to an individual who suffers said disorder, or for evaluating the predisposition of an individual presenting a prodromal symptom to develop said disorder, based on the use of the brain-derived neutrophic factor (BDNF) as a marker.

5 Claims, 1 Drawing Sheet

METHODS FOR DIAGNOSIS AND PROGNOSTIC OF PSYCHIATRIC DISEASES

CROSS-REFERENCE TO RELATED APPLICATIONS

This application claims the priority of Spanish Patent Application No. P200602139.7 filed on Aug. 4, 2006.

FIELD OF THE INVENTION

The invention is comprised within the field of psychiatric disorders occurring with psychosis, particularly schizophrenia and bipolar disorder, and relates to the use of the brain-derived neutrophic factor (BDNF) as a marker for the diagnosis of said mentioned disorders and to the use of expression enhancing substances of said factor for the treatment of said disorders.

BACKGROUND OF THE INVENTION

Psychoses are a group of behavioral, judgment and perception disorders with an emotional or organic origin in which the person loses touch with reality. Their durations, characteristics and treatments all differ. They are usually chronic disorders and can occur with a severe and very dysfunctional symptomatology.

Schizophrenia is a mental disorder affecting 1% of the world population and is characterized by a loss of judgment of reality and a personality disorder, probably due to a biochemical or microstructural brain defect that has not yet been well determined. There is a wide variety of symptoms indicative of schizophrenia, including thought disorders, hallucinations, abnormal movements and amotivational behavior. None of these symptoms is pathognomic of the disorder, which makes diagnosis difficult. It has an unknown cause although it is though that several factors are involved in its onset, including genetic heritage, disorders in cell population migration during embryonic development, drug abuse and environmental stress. It is a chronic disease but improves with treatment, especially with drugs.

As in many mental disorders, the diagnosis of schizophrenia is based on the behavior of the person being evaluated. There is a list of criteria that a person must meet in order to be diagnosed with the disorder and these criteria depend on the presence and duration of certain signs and symptoms.

The most widely used criteria to diagnose schizophrenia are set forth in the DSM, *Diagnostic and statistical manual of mental disorders* of the American Psychiatry Association and the World Health Organisation: International Statistical Classification of Illnesses and related Health Problems (ICD)]. The most recent versions are ICD-10 and DSM-IV-TR.

In order to be diagnosed with schizophrenia a person must exhibit a series of characteristic symptoms for several months. There are no biological markers with a diagnostic, at the onset thereof, or prognostic value for this disorder. This shortcoming is very limiting because various psychiatric disorders start with similar symptoms. This is why it is very difficult to initially distinguish schizophrenia from other mental disorders, such as bipolar disorder or manic-depressive disorder, major depression or other nonspecified psychoses. People whose symptoms cannot be clearly classified sometimes receive the diagnosis of "schizoaffective disorder".

In addition, bipolar disorder (also referred to as type I bipolar disorder) occurs with episodes of mania and depression and may also present psychosis at the onset thereof. This disorder affects about 2% of the world population and its correct diagnosis is done according to the criteria described in ICD-10 and DSM-IV-TR; however, said diagnosis may take up to several years after the first episode. Once bipolar disorder is diagnosed it can be effectively treated.

Until now no biological markers have been described which allow a differential diagnosis of severe psychoses (schizophrenia and bipolar disorder) and of other nonspecified psychoses. The diagnosis of such disorders at the onset of symptoms is extremely important for establishing a suitable treatment that can improve the evolution of the disorder in the long term for the patients.

Specifically, biological markers of the possible evolution of the psychosis have not been identified [Freedman R., 2005. Early biomarkers of psychosis. Dialogues Clin Neurosci. 7:17-29]. This could be because of the many complex underlying factors of schizophrenia, bipolar disorder and other psychoses. Although genotypes and phenotypes associated with these disorders have been described, some of which become apparent at early ages, they have little predictive value.

In linkage and association studies, it has been found that chromosomal regions 1q, 5p, 5q, 6p, 6q, 8p, 10p, 13q, 15q and 22q contain schizophrenia risk genes which could not always be replicated in all the studied populations [Berry N. et al., 2003. Molecular genetics of schizophrenia: a critical review. J Psychiatry Neurosci. 28:415-429]. In addition, neuregulin gene 1 (NRG1) is perhaps the gene that is most clearly associated with schizophrenia; however levels of this neuregulin cannot be detected in blood, and its genetic variants and polymorphisms are not well determined [Corfas G. et al., 2004. Neuregulin 1-erbB signaling and the molecular/cellular basis of schizophrenia. Nat Neurosci. 7:575-580].

As regards bipolar disorder, a number of genetic studies have been conducted which have been useful in establishing several loci associated to this disorder, including 4q31, 6q24 and 1p35-p36 [Schumacher J et al., 2005. Genomewide scan and fine-mapping linkage studies in four European samples with bipolar affective disorder suggest a new susceptibility locus on chromosome 1p35-p36 and provides further evidence of loci on chromosome 4q31 and 6q24. Am J Hum Genet. 77:1102-1111]. Immune system disorders which are detectable in manic episodes manic episodes in bipolar patients, however it has not been determined if these values are altered at the onset of the disorder [Liu HC et al., 2004. Immunologic variables in acute mania of bipolar disorder. J. Neuroimmunol. 150:116-122]. Disorders in the transferrin receptor have been observed in mania periods, but this parameter has not been assessed either in the first psychotic episode in these patients [Tsai SY et al., 2003. Plasma levels of soluble transferrin receptors and Clara cell protein (CC16) during bipolar mania and subsequent remission. J Psychiatr Res. 37:229-235].

It has now surprisingly been found that the brain-derived neutrophic factor or BDNF can be used as a molecular marker for the diagnosis of psychiatric disorders occurring with psychosis, e.g. schizophrenia and bipolar disorder. No diagnostic or therapeutic application of BDNF is known today.

BDNF is the most abundant neurotrophin in the brain, where it promotes growth and maintenance of intercellular junctions, is useful as a modulator of neurotransmitter signals and participates in plasticity mechanisms such as long-term potentiation and learning. Accordingly, BDNF signaling anomalies can affect neuronal differentiation and synaptic communication and thus alter brain development and function.

BDNF is the expression product of the BDNF gene, a gene induced by cortical neurons and necessary for survival of neurons of the striatum in the brain. The expression of said BDNF gene is reduced in patients suffering Alzheimer's disease and Huntington's disease. This gene seems to have some role in regulating the response to stress.

Plasma levels of BDNF in chronic schizophrenics have been studied, with different results according to the different groups of patients studied [Jockers-Scherübl M C., et al., 2004. Brain-derived neurotrophic factor serum concentrations are increased in drug-naive schizophrenic patients with chronic cannabis abuse and multiple substance abuse. Neurosci. Lett. 371, 79-83; Pirildar S., et al., 2004. Low serum levels of brain-derived neurotrophic factor in patients with schizophrenia do not elevate after antipsychotic treatment. Prog. Neuropsychopharmacol. Biol. Psychiatry. 28, 709-713; Toyooka K., et al., 2002. Decreased levels of brain-derived neurotrophic factor in serum of chronic schizophrenic patients. Psychiatr. Res. 110, 249-257]. However, said levels have not been determined in patients suffering the first psychotic episode, as described in the present invention.

SUMMARY OF THE INVENTION

The main object of the present invention is to provide an in vitro method for detecting a psychiatric disorder occurring with psychosis selected from schizophrenia and bipolar disorder, in an individual who has suffered a first psychotic episode, or for determining the state or severity of said disorder in said individual, or for monitoring the effect of a therapy administered to an individual who suffers said disorder. An additional object consists of providing compounds for the treatment of said psychiatric disorders occurring with psychosis, particularly schizophrenia or bipolar disorder.

The inventors have now surprisingly found that plasma levels of BDNF decrease in the first psychotic episodes. This decrease is much greater in individuals who will later develop schizophrenia or bipolar disorder. Therefore, the reduction of the plasma levels of BDNF in the first psychotic symptoms of schizophrenia and of bipolar disorder is a novel milestone in establishing early diagnosis of said mental disorders. As is known, BDNF crosses the blood-brain barrier, so plasma levels of said factor can reflect the cerebral levels thereof.

The measurement of plasma levels of BDNF during the first psychotic episode is information that has tremendous diagnostic value, since the concentration of that factor is very low in schizophrenics and bipolar patients. Diagnosis at the onset of symptoms is important for establishing a suitable treatment that can improve long-term evolution of such patients. The assessment of plasma levels of BDNF when prodromal symptoms occur, i.e. prior to the first psychotic episode, such as, for example, loss of interest in work and social activity, neglected personal appearance and hygiene, general anxiety and moderate degrees of depression and concern, may be important for determining the risk if suffering these disorders and establishing therapeutic regimen preventing the psychosis.

Accordingly, the invention relates to the use of BDNF as a biological marker for the early diagnosis of a psychiatric disorder occurring with psychosis, such as schizophrenia or bipolar disorder, in an individual who has suffered a first psychotic episode, or for determining the state or severity of said disorder in said individual, or for monitoring the effect of a therapy in an individual who suffers said disorder, or for evaluating the predisposition of an individual presenting a prodromal symptom to develop a psychiatric disorder occurring with psychosis such as schizophrenia or bipolar disorder.

The invention also generally relates to the use of said biological marker for the search, identification, development and evaluation of the efficacy of compounds for the treatment of a psychiatric disorder occurring with psychosis, such as schizophrenia or bipolar disorder, for the purpose of developing new drugs. The invention further relates to the use of compounds which promote the expression of BDNF. In a particular embodiment, the methods and compounds of the present invention are applied when the first psychotic episodes occur and/or in individuals showing prodromal signs prior to the triggering of said psychiatric disorders.

Therefore, in one aspect, the invention relates to an in vitro method for detecting (diagnosing) a psychiatric disorder occurring with psychosis selected from schizophrenia and bipolar disorder, in an individual who has suffered a first psychotic episode, or for determining the state or severity of said disorder in said individual, or for monitoring the effect of a therapy administered to an individual who suffers said disorder, or for evaluating the predisposition of an individual presenting a prodromal symptom to develop a psychiatric disorder occurring with psychosis, such as schizophrenia or bipolar disorder.

In another aspect, the invention relates to the use of a BDNF peptide sequence, or of a nucleotide sequence of the BDNF gene (or its complementary chain) or of antibodies capable of binding to said factor or to a fragment thereof containing an antigenic determinant specific for said factor for detecting (diagnosing) in vitro a psychiatric disorder occurring with psychosis, e.g. schizophrenia or bipolar disorder, or for evaluating the predisposition of an individual presenting a prodromal symptom to develop a psychiatric disorder occurring with psychosis, such as schizophrenia or bipolar disorder.

In another aspect, the invention relates to a method for the screening, search, identification, development and evaluation of the efficacy of compounds for the treatment of a psychiatric disorder occurring with psychosis selected from schizophrenia and bipolar disorder.

In another aspect, the invention relates to the use of (i) a nucleotide sequence of the BDNF gene, or of (ii) a BDNF amino acid sequence, or of (iii) an antibody capable of binding to BDNF or to a fragment thereof containing an antigenic determinant, in a method for the screening, search, identification, development and evaluation of the efficacy of compounds for the treatment of a psychiatric disorder occurring with psychosis, such as schizophrenia or bipolar disorder.

In another aspect, the invention relates to an in vitro method for the identification and evaluation of the efficacy of the treatment of a psychiatric disorder occurring with psychosis, e.g. schizophrenia or bipolar disorder, comprising the quantification of the level of BDNF or the quantification of the level of expression of the BDNF gene in the same individual throughout the different phases or stages of the disorder, or during periods of treatment and of absence thereof, and its comparison with control values considered normal or with prior values of the same patient.

In another aspect, the invention relates to a pharmaceutical composition comprising a therapeutically effective amount of a compound which blocks the inhibition of the expression or activity of BDNF, or of a compound which promotes or enhances the expression of said BDNF, together with one or more pharmaceutically acceptable excipients and/or carriers.

In another aspect, the invention relates to the use of a compound which blocks the inhibition of the expression or activity of BDNF, or of a compound which promotes or enhances the expression of said BDNF, in preparing a pharmaceutical composition for the prevention and/or treatment of psychiatric disorders occurring with psychosis, e.g. schizophrenia or bipolar disorder.

In another aspect, the invention relates to a kit, such as a kit suitable for detecting a psychiatric disorder occurring with psychosis, e.g. schizophrenia or bipolar disorder, in an individual who has suffered a first psychotic episode, or for determining the state or severity of said disorder in said individual, or for monitoring the effect of the therapy administered to an individual presenting said disorder, or for evaluating the predisposition of an individual presenting a prodromal symptom to develop a psychiatric disorder, such as those previously mentioned.

DETAILED DESCRIPTION OF THE INVENTION

Figure 1:
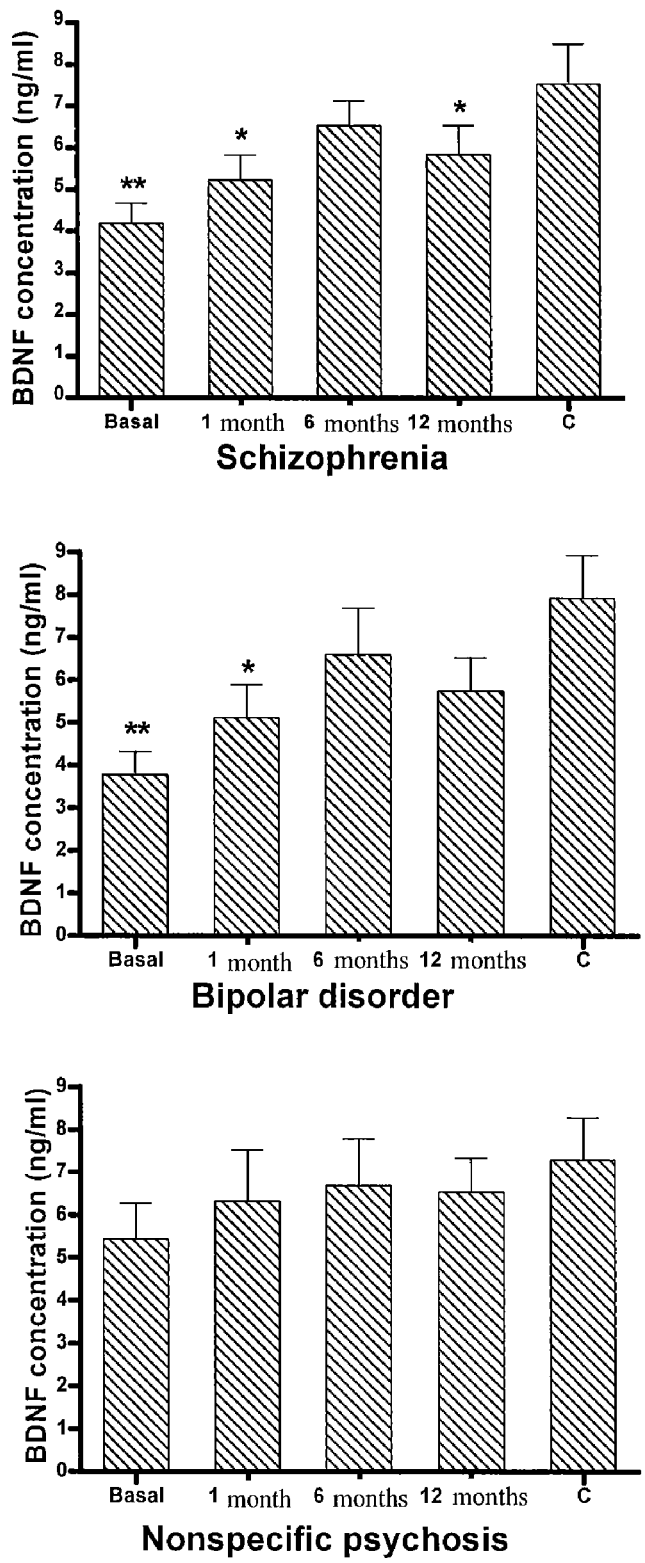
FIG. 1 is a set of graphs showing the plasma concentration of BDNF in patients with schizophrenia, bipolar disorder and other nonspecified psychoses, and healthy controls (C), at different times. The levels of BDNF were measured by ELISA and the comparisons were done by means of pairing patients with controls of the same age and sex. *p<0.05 and **p<0.01.

In order to aid in understanding the invention object of this patent application, the meaning of some terms and expressions in the context of the invention is provided below:

The term "individual" refers to a member of an animal species, and includes but is not limited to domestic animals, primates and humans; the subject is preferably a human being, male or female, of any age or race.

The expressions "schizophrenia" and "bipolar disorder" refer to psychiatric disorders diagnosed by means of the "Structured Clinical Interview for DSM-IV" (Diagnostic and Statistical Manual of Mental Disorders, 4th Edition), SCID-I test; the term "schizophrenia" includes all the subtypes of schizophrenia accepted by the scientific community and comprised in said publication (e.g. paranoid type, disorganized type, catatonic type, undifferentiated type and residual type).

The expression "psychiatric disorder occurring with psychosis" refers to psychiatric disorders in which the psychosis indicates the presence of hallucinations, of delirious ideas or of a limited number of clearly abnormal behaviors, such as extreme excitation or hyperactivity, severe and prolonged social isolation not due to depression or anxiety, marked psychomotor inhibition or catatonic manifestations (CIE 10).

The term "protein" refers to a molecular chain of amino acids, bound by covalent or non-covalent bonds. The term includes all forms of post-translational modifications, for example glycosylation, phosphorylation or acetylation.

The term "antibody" refers to a protein with ability of specific binding to an "antigen". The term "antibody" comprises monoclonal or polyclonal antibodies, intact or fragments thereof preserving the ability to bind to the antigen, recombinant antibodies, combibodies, etc., either human or humanized and of a non-human origin.

As it is used in the present invention, the term "oligonucleotide primer" refers to a nucleotide sequence, which is complementary to a nucleotide sequence of the BDNF gene encoding for BDNF. Each primer hybridizes with its target nucleotide sequence and acts as a starting point for DNA polymerization.

The present invention is based on the discovery that the expression of BDNF and, accordingly, of the gene encoding for said factor, is reduced in individuals who suffered a first psychotic episode and who one year later were diagnosed with schizophrenia or bipolar disorder, with regard to control individuals.

Accordingly, the evaluation and comparison of the level of BDNF, and of the BDNF gene, in a biological sample from an individual can be used for the purposes of diagnosis, prognosis or prevention of psychiatric disorders occurring with psychosis in general, and of schizophrenia or bipolar disorder in particular. By way of illustration, a reduced level of said molecular marker in an individual who has suffered a first psychotic episode with regard to the level of said molecular marker in control individuals (i.e. individuals with no medical history of psychiatric disorders occurring with psychosis, e.g. schizophrenia or bipolar disorder) or with normal reference values (generally obtained from control individuals) is indicative of a psychiatric disorder occurring with psychosis, particularly schizophrenia or bipolar disorder, or of a major risk or predisposition of a subject to develop said disorder. The comparison of the levels of said markers, at any given time, in an individual, diagnosed or not with said psychiatric disorder occurring with psychosis, e.g. schizophrenia or bipolar disorder, with those of the prior samples of the same individual can be indicative of the evolution and prognosis of said disorder or of the individual's predisposition to develop said disorder.

The aforementioned finding can be used, among other applications, in diagnostic assays or in assays for evaluating the risk or predisposition of an individual to develop a psychiatric disorder occurring with psychosis, e.g. schizophrenia or bipolar disorder, in prognostic assays, in assays for monitoring the effect of the therapy administered to an individual to analyze the efficacy of the therapy and the evolution of the disorder, and in assays for screening compounds potentially useful for the treatment of psychiatric disorders occurring with psychosis, e.g. schizophrenia or bipolar disorder.

The invention accordingly provides a method for detecting and quantifying the expression of the BDNF gene and/or the expression of its expression product, BDNF. The invention also provides methods for detecting interactions between said products and other compounds, for example, enhancers of the expression of BDNF.

Therefore, in one aspect the invention relates to an in vitro method, hereinafter method of the invention, for detecting a psychiatric disorder occurring with psychosis selected from schizophrenia and bipolar disorder, in an individual who has suffered a first psychotic episode, or for determining the state or severity of said disorder in said individual, or for monitoring the effect of a therapy administered to an individual who suffers said disorder, comprising:

a) quantifying the level of the brain-derived neutrophic factor (BDNF) in a sample from said individual; and b) comparing said level with that of a control sample;

wherein a decrease in said level with regard to the level in the control sample is indicative of schizophrenia or bipolar disorder; or, alternatively, a) quantifying the level of expression of the gene encoding for the brain-derived neutrophic factor (BDNF) [BDNF gene] in a sample from said individual; and b) comparing said level with that of a control sample;

wherein a decrease in said level with regard to the level in the control sample is indicative of schizophrenia or bipolar disorder.

The method of the invention has high sensitivity and specificity, and is based on the fact that individuals who suffered a first psychotic episode and who one year later were diagnosed with schizophrenia or bipolar disorder present reduced levels of BDNF, in comparison with the level of BDNF in samples from control individuals with no medical history of psychiatric disorders occurring with psychosis, e.g. schizophrenia or bipolar disorder.

To put the method of the invention into practice, a biological sample is obtained from the individual to be studied. Said biological sample can be obtained in the same laboratory in which the method is going to be performed or in another center and later sent to the laboratory for study. Illustrative, non-limiting examples of said samples include different types of biological fluids, such as blood, cerebrospinal fluid, peritoneal fluid, feces, urine and saliva, as well as tissue samples. The biological fluid samples can be obtained by any conventional method, as can the tissue samples; by way of illustration, said tissue samples can be biopsy samples obtained by surgical resection. The samples can be obtained from previously diagnosed individuals (patients) with a psychiatric disorder occurring with psychosis, e.g. schizophrenia or bipolar disorder, or from individuals not diagnosed with said disorder, or from patients under treatment for said disorder, or from patients who have previously been treated.

In a particular embodiment, the method of the invention comprises quantifying the level of BDNF in a sample from said individual and its comparison with that of a control sample, wherein a decrease in said level with regard to the level in the control sample is indicative of schizophrenia or bipolar disorder.

The level (concentration) of said BDNF can be quantified by means of any conventional method which allows detecting and quantifying said factor (protein) in a sample from an individual. In this case, the method of the invention includes a prior extraction step for the purpose of obtaining a protein extract containing said factor, which can be done by means of conventional techniques (Chomczynski et al., Anal. Biochem., 1987, 162:156; Chomczynski P., Biotechniques, 1993, 15:532).

Virtually any conventional method can be used within the invention for detecting and quantifying the level of BDNF. By way of non-limiting illustration, the level of said protein can be quantified by means of the use of any conventional method known by the person skilled in the art, for example, by means of the use of antibodies capable of binding to BDNF (or to a fragment thereof containing an antigenic determinant) and subsequent quantification of the complexes formed. The antibodies which are used in these assays can be labeled or unlabeled. Illustrative examples of labels which can be used include radioactive isotopes, enzymes, fluorophores, chemiluminescent reagents, enzymatic substrates or cofactors, enzymatic inhibitors, particles, dyes, etc. There is a wide variety of known assays which can be used in the present invention, using unlabeled antibodies (primary antibody) and labeled antibodies (secondary antibody); these techniques include Western-blot, ELISA (Enzyme-Linked ImmunoSorbent Assay), RIA (radioimmunoassay), competitive EIA (competitive enzymatic immunoassay), DAS-ELISA (double antibody sandwich ELISA), immunocytochemical and immunohistochemical techniques, techniques based on the use of protein biochips or microarrays including specific antibodies or assays based on colloidal precipitation in formats such as dipsticks. Other ways of detecting and quantifying said EAAT1, EAAT2 or EGF proteins include affinity chromatography techniques, ligand binding assays, etc.

In a particular embodiment, the quantification of the level of BDNF is carried out by means of the use of antibodies capable of binding to BDNF (or to a fragment thereof containing an antigenic determinant) and subsequent quantification of the complexes formed, for example, by means of immunochemical techniques which allow quantifying the antigen-antibody binding, for example, Western blot, ELISA, protein biochips, etc.; the quantification of the level of BDNF is preferably carried out by means of ELISA using suitable antibodies capable of binding to said factor [there are commercial antibodies capable of binding to said proteins (see the Example attached to this description)].

In another particular embodiment, the method of the invention comprises quantifying the level of expression of the BDNF gene, in a sample from said individual and its comparison with that of a control sample, wherein a decrease in said level with regard to the level of expression of the BDNF gene in the control sample is indicative of schizophrenia or bipolar disorder.

As is known, the level of expression of a gene can be quantified by means of quantifying the level of mRNA encoding said gene, or, alternatively, the level of the complementary DNA (cDNA) to said mRNA. In this case, the method of the invention includes a prior extraction step for the purpose of obtaining the total RNA, which can be done by means of conventional techniques (Chomczynski et al., Anal. Biochem., 1987, 162:156; Chomczynski P., Biotechniques, 1993, 15:532).

Virtually any conventional method can be used in the invention for detecting and quantifying the level of mRNA encoding BDNF or its corresponding cDNA. By way of non-limiting illustration, the level of mRNA encoding said BDNF can be quantified by means of the use of conventional methods, for example, methods comprising the mRNA amplification and the quantification of said mRNA amplification product, such as electrophoresis and staining, or alternatively by means of Southern blot and the use of suitable probes, Northern blot and use of probes specific for the mRNA of the gene of interest (BDNF) or its corresponding cDNA, mapping with nuclease S1, RT-LCR, hybridization, microarrays, etc., preferably, by means of quantitative real time PCR using a suitable label.

Similarly, the level of the corresponding cDNA to said mRNA encoding BDNF can also be quantified by means of the use of conventional techniques; in this case, the method of the invention includes a synthesis step to synthesize the corresponding cDNA by means of reverse transcription (RT) of the corresponding mRNA followed by amplification and quantification of said cDNA amplification product; in a particular embodiment, the amplification is carried out qualitatively or quantitatively by means of PCR, using oligonucleotide primers specifically amplifying regions of the BDNF gene.

The method of the invention also comprises the step of comparing the level of expression of BDNF or of the BDNF gene determined in the sample from the individual object of study with the levels of a control sample (e.g. with the reference values). The level of BDNF and the level of expression of the BDNF gene, can be determined by the previously mentioned techniques in samples from individuals without psychiatric disorders occurring with psychosis, e.g. schizophrenia or bipolar disorder. A decrease in the level of BDNF or in the level of expression of BDNF in the sample from the individual object of study with regard to the corresponding levels in the control sample is indicative of schizophrenia or bipolar disorder.

The investigators have additionally discovered that the expression of BDNF and, accordingly, of the gene encoding for said factor, is also reduced in individuals presenting a prodromal syndrome, so said factor can also be used as a marker indicative of the predisposition of said individual to develop a psychiatric disorder occurring with psychosis, such as schizophrenia or bipolar disorder.

Therefore, in another aspect, the invention relates to an in vitro method for evaluating the predisposition of an individual presenting a prodromal symptom to develop a psychiatric disorder occurring with psychosis selected from schizophrenia and bipolar disorder, comprising:

a) quantifying the level of the brain-derived neutrophic factor (BDNF) in a sample from said individual; and b) comparing said level with the level of a control sample;

wherein a decrease in said level with regard to the level in the control sample is indicative of a predisposition to develop schizophrenia or bipolar disorder; or, alternatively, a) quantifying the level of expression of the BDNF gene encoding for the brain-derived neutrophic factor (BDNF) in a sample from said individual; and b) comparing said level with the level of a control sample;

wherein a decrease in said level with regard to the level in the control sample is indicative of a predisposition to develop schizophrenia or bipolar disorder.

To put this method into practice, a sample from an individual presenting one or more prodromal symptoms is analyzed. As mentioned above, prodromal symptoms are the symptoms prior to the onset of the first psychotic episode; non-limiting illustrative examples of such symptoms include loss of interest in work, loss of interest in social activity, neglected personal appearance, neglected personal hygiene, general anxiety, a moderate degree of depression, a moderate degree of concern, etc., all of which are well known by persons skilled in the art. In a particular embodiment, the prodromal symptom is selected from the group formed by loss of interest in work, loss of interest in social activity, neglected personal appearance, neglected personal hygiene, general anxiety, a moderate degree of depression, a moderate degree of concern, and combinations thereof.

The quantification of BDNF or of the level of expression of the BDNF gene in a sample from said individual, as well as its comparison with the corresponding levels in a control sample can be carried out as described above.

The nucleotide sequence of the BDNF gene (or its complementary chain) as well as the amino acid sequence of BDNF and antibodies capable of binding to said factor or to a fragment thereof containing an antigenic determinant specific for said factor can be used for detecting (diagnosing) in vitro a psychiatric disorder occurring with psychosis, e.g. schizophrenia or bipolar disorder, in an individual who has suffered a first psychotic episode, or for determining in vitro the state or severity of said disorder in said individual, or for determining in vitro the effect of the treatment in an individual presenting said disorder, or for evaluating the predisposition of an individual presenting a prodromal symptom to develop a psychiatric disorder occurring with psychosis, such as schizophrenia or bipolar disorder.

Therefore, in another aspect, the invention relates to the use of a BDNF peptide sequence for detecting (diagnosing) in vitro a psychiatric disorder occurring with psychosis, e.g. schizophrenia or bipolar disorder, in an individual who has suffered a first psychotic episode, or for determining in vitro the state or severity of said disorder in said individual, or for determining in vitro the effect of the treatment in an individual presenting said disorder, or for evaluating the predisposition of an individual presenting a prodromal symptom to develop a psychiatric disorder occurring with psychosis, such as schizophrenia or bipolar disorder. In a particular embodiment, said psychiatric disorder occurring with psychosis is schizophrenia or bipolar disorder. Said peptide sequence can be a sequence comprising an epitope of said BDNF.

In another aspect, the invention relates to the use of a polynucleotide or nucleotide sequence of the BDNF gene (or of its complementary chain) for detecting (diagnosing) in vitro a psychiatric disorder occurring with psychosis, e.g. schizophrenia or bipolar disorder, in an individual who has suffered a first psychotic episode, or for determining in vitro the state or severity of said disorder in said individual, or for determining in vitro the effect of the treatment in an individual presenting said disorder, or for evaluating the predisposition of an individual presenting a prodromal symptom to develop a psychiatric disorder occurring with psychosis, such as schizophrenia or bipolar disorder. In a particular embodiment, said psychiatric disorder occurring with psychosis is schizophrenia or bipolar disorder. Said nucleotide sequence can be a probe complementary to a nucleotide sequence present in said BDNF gene useful for detecting the corresponding nucleotide sequence of said gene.

In another aspect, the invention likewise relates to the use of an antibody capable of binding to BDNF, or to a fragment thereof containing an antigenic determinant of said factor, for detecting (diagnosing) in vitro a psychiatric disorder occurring with psychosis, e.g. schizophrenia or bipolar disorder, in an individual who has suffered a first psychotic episode, or for determining in vitro the state or severity of said disorder in said individual, or for determining in vitro the effect of the treatment in an individual presenting said disorder, or for evaluating the predisposition of an individual presenting a prodromal symptom to develop a psychiatric disorder occurring with psychosis, such as schizophrenia or bipolar disorder. Said antibodies can be recombinant antibodies, monoclonal antibodies, polyclonal antibodies, intact or fragments thereof preserving the ability to bind to said BDNF, for example, Fab, scFv fragments, etc., human antibodies, humanized antibodies or antibodies of non-human origin. In a particular embodiment, said psychiatric disorder occurring with psychosis is schizophrenia or bipolar disorder.

Additionally, said nucleotide sequence of the BDNF gene, as well as said BDNF amino acid sequence and said antibody capable of binding to said BDNF (or to a fragment thereof containing an antigenic determinant) can be used in the screening, search, identification, development and evaluation of the efficacy of compounds for the treatment of psychiatric disorders occurring with psychosis, e.g. schizophrenia or bipolar disorder.

Therefore, in another aspect, the invention relates to a method for the screening, search, identification, development and evaluation of the efficacy of compounds for the treatment of psychiatric disorders occurring with psychosis, e.g. schizophrenia or bipolar disorder, comprising (i) putting an expression system expressing the BDNF gene into contact with the compound to be tested, (ii) evaluating the expression of said gene, and (iii) selecting that compound which promotes, increases or enhances expression (overexpression) of said BDNF gene since said compound would be a compound potentially useful for the treatment of psychiatric disorders occurring with psychosis, particularly schizophrenia or bipolar disorder. Said expression system can be, virtually, any cell naturally or recombinantly expressing the BDNF gene. The expression of said gene can be evaluated by any conventional method, for example, by means of quantifying the mRNA expressing said gene or its corresponding cDNA, or by means of quantifying BDNF by any of the methods mentioned above. When a compound increases the expression of BDNF, said compound becomes a candidate compound potentially useful for the treatment of psychiatric disorders occurring with psychosis, e.g. schizophrenia or bipolar disorder, particularly a candidate compound potentially useful for the treatment of the first psychotic episode or of those individuals showing prodromal signs prior to the triggering of said mental disorders, e.g. schizophrenia or bipolar disorder.

Additionally, in another aspect the invention relates to the use of (i) a nucleotide sequence of the BDNF gene, or of (ii) a BDNF amino acid sequence, or of (iii) an antibody capable of binding to BDNF (or to a fragment thereof containing an antigenic determinant), in a method for the screening, search, identification, development and evaluation of the efficacy of compounds for the treatment of psychiatric disorders occurring with psychosis, e.g. schizophrenia or bipolar disorder.

In another aspect, the invention relates to an in vitro method for the identification and evaluation of the efficacy of the treatment of a psychiatric disorder occurring with psychosis, e.g. schizophrenia or bipolar disorder, in an individual who has suffered a first psychotic episode and has been diagnosed with said disorder. The method contemplates the quantification of the level of BDNF or of the level of expression of the BDNF gene in the same individual throughout the different phases or stages of the disorder, or during periods of treatment and of absence thereof, and its comparison with control values considered normal or with prior values of the same patient. When an agent increases the level of BDNF or increases the expression of the BDNF gene, said agent becomes a candidate compound for the treatment of psychiatric disorders occurring with psychosis, e.g. schizophrenia or bipolar disorder.

The compounds which block the inhibition of the expression or activity of BDNF, as well as the compounds which promote or enhance the expression of said BDNF, can be used in the treatment of psychiatric disorders occurring with psychosis, e.g. schizophrenia or bipolar disorder, particularly, in the treatment of the first psychotic episode and of individuals showing prodromal signs prior to the triggering of the mental disorder. Illustrative non-limiting examples, of said compounds include cytotoxic agents, chemotherapeutic agents, including organic and inorganic molecules, peptides, phosphopeptides, antibiotics and generally any compound which promotes the expression of BDNF, i.e. positive modulators of the expression of said factor, such as, for example, progesterone, fluoxetine, desipramine and other antidepressants increasing the expression of BDNF.

In another aspect, the invention relates to a pharmaceutical composition comprising a therapeutically effective amount of a compound which blocks the inhibition of the expression or activity of BDNF, or of a compound which promotes or enhances the expression of said BDNF, together with one or more pharmaceutically acceptable excipients and/or carriers. Illustrative non-limiting examples of said compounds which block the inhibition of the expression or activity of BDNF, or of compounds which promote or enhance the expression of said BDNF include cytotoxic agents, chemotherapeutic agents, including organic and inorganic molecules, peptides, phosphopeptides, antibiotics and in general compounds which promote the expression of BDNF. In a particular embodiment, said pharmaceutical composition comprises a positive modulator of the expression of said BDNF.

The excipients, carriers and auxiliary substances must be pharmaceutically and pharmacologically tolerable and must be able to be combined with other formulation or preparation components and not have any adverse effect on the treated subject. The pharmaceutical compositions can be presented in any suitable form of administration, for example, in pharmaceutical forms suitable for oral and parenteral administration (including, e.g. intravenous, subcutaneous, intradermal, intramuscular, intraperitoneal and intrathecal administration). The formulations can be single-dose formulations and will be prepared according to classic Galenic methods. A review of the different pharmaceutical administration forms of drugs and of their preparation can be found in the book "Tratado de Farmacia Galánica", C. Faulí i Trillo, 10 Edition, 1993, Luzán 5, S.A. de Ediciones.

In another aspect, the invention relates to the use of a compound which blocks the inhibition of the expression or activity of BDNF, or of a compound which promotes the expression of said BDNF, in preparing a pharmaceutical composition for the prevention and/or the treatment of psychiatric disorders occurring with psychosis, e.g. schizophrenia or bipolar disorder; particularly the pharmaceutical composition provided by this invention can be very useful for treating individuals who present a prodromal symptom or who have suffered a first psychotic episode for the purpose of preventing the development of psychiatric disorders occurring with psychosis, e.g. schizophrenia or bipolar disorder.

In another aspect, the invention relates to a kit, hereinafter kit of the invention, useful for putting the methodology described herein into practice. Therefore, said kit can contain the reagents necessary for detecting the level of BDNF, or for detecting the level of expression of mRNA expressing BDNF, or its corresponding cDNA, including:

a) an antibody capable of binding to BDNF, or to a fragment thereof containing an antigenic determinant; and/or b) a pair of oligonucleotide primers for specifically amplifying a fragment of the mRNA or of the cDNA encoding BDNF.

The kit of the invention can be used for detecting a psychiatric disorder occurring with psychosis, e.g. schizophrenia or bipolar disorder, in an individual who has suffered a first psychotic episode, or for determining the state or severity of said disorder in said individual, or for monitoring the effect of the therapy administered to a subject presenting said disorder, or for evaluating the predisposition of an individual presenting a prodromal symptom to develop a psychiatric disorder occurring with psychosis, such as schizophrenia or bipolar disorder.

The following example illustrates the invention though it should not be considered to limit it.

EXAMPLE 1

Identification of BDNF as a Biological Marker for the Early Diagnosis of Schizophrenia or Bipolar Disorder Materials and Methods 48 patients of 23.7±1 years of age (mean±SEM) who suffered their first psychotic episode during the years 2002-2004 were studied. They all gave their informed consent to participate in the study. These patients were diagnosed 12 months after the first psychotic episode by means of the "Structured Clinical Interview for DSM-IV" (Diagnostic and Statistical Manual of Mental Disorders, 4th Edition), SCID-I test. 21 patients were diagnosed with schizophrenia, 14 with bipolar disorder and the other 13 with nonspecified psychotic disorders.

The blood samples were extracted upon arrival to the Emergency Room and after 1, 6 and 12 months, in tubes containing K3-EDTA [tripotassium salt of ethylenediaminetetraacetic acid]. The plasma was isolated by means of centrifugation at 300 g for 10 minutes and was frozen at −80° C.

until its use. Blood was also extracted from 43 healthy volunteers of 25.5±0.8 years of age (mean±SEM) who, in the analysis process, were paired by age and sex and were used as controls. All the patients and controls were recruited from the same community. Subjects with a mental retardation, organic brain disorders or who used drugs were excluded from the study.

Plasma levels of BDNF and tumor necrosis factor-alpha [TNFα] (the latter is used as a control) were measured in duplicate by means of ELISA with a commercial kit (CYT306 of Chemicon and KHC3011C of Biosource International, respectively). The intensity of the signal was measured by means of determining the absorbance in a microplate reader (BIO-TEK, Sinergy HT), with a wavelength of 450 nm. The values included in the histograms represent the mean±SEM and the statistical analysis was calculated by means of comparisons between groups, and between each group of patients and controls using repeated measures ANOVA.

Results and Discussion

Plasma levels of BDNF decreased in the patients with first psychotic episode and who one year later were diagnosed with schizophrenia or with bipolar disorder (45% and 52% respectively, $p<0.01$) (FIG. 1). In turn, the patients with non-specified psychoses also had said levels reduced but to a lesser extent (25%, not statistically significant). Oddly enough, the BDNF values progressively increased in the schizophrenic and bipolar patients after the first psychotic episode during the first year of treatment. In contrast, plasma levels of TNFα did not change, in comparison with their controls, in all the studied patient groups, which is consistent with the findings of other investigators [Baker I. et al., 1996. Serum cytokine concentrations in patients with schizophrenia. Schizophr. Res. 20, 199-203].

The results explained indicate that plasma levels of BDNF are associated with the onset of schizophrenia and bipolar disorder, and are consistent with the hypothesis that a deficiency of this neutrophic factor may contribute to the underlying structural and functional damage of these disorders [Durany N. & Thome J., 2004. Neurotrophic factors and the pathophysiology of schizophrenic psychoses. Eur. Psychiatry. 19, 326-337]. Furthermore, the similar reduction of levels of BDNF in schizophrenia and in bipolar disorder is reminiscent of other clinical and neurobiological findings in both disorders, and it supports the idea that both disorders share similar molecular mechanisms [Gonzalez-Pinto A. et al., 2003. Age-dependence of Schneiderian psychotic symptoms in bipolar patients. Schizophr. Res. 61, 157-162].

The invention claimed is:

1. An in vitro method for detecting a psychiatric disorder occurring with psychosis selected from schizophrenia and bipolar disorder in an individual who has suffered a first psychotic episode but has not previously been diagnosed with schizophrenia or bipolar disorder comprising:
    a) quantifying the level of the brain-derived neutrophic factor (BDNF) in a sample from said individual;
    b) quantifying the level of BDNF in a control sample, wherein a decrease in the level of BDNF in the sample from the individual with regard to the level in the control sample is indicative of schizophrenia or bipolar disorder.

2. A method according to claim 1, wherein said sample is selected from the group consisting of blood, serum, plasma, urine, saliva, feces, cerebrospinal fluid, peritoneal fluid and a tissue sample.

3. A method according to claim 1, comprising subjecting said sample to an extraction process for obtaining an extract comprising a protein extract.

4. A method according to claim 1, wherein said sample is plasma.

5. A method according to claim 1, wherein the quantification of the level of said BDNF is carried out by means of antibodies capable of binding to said factor or to a fragment thereof containing an antigenic determinant, and using immunochemical techniques for quantifying antigen-antibody binding.

* * * * *